United States Patent [19]

Fellows et al.

[11] Patent Number: 4,752,496

[45] Date of Patent: Jun. 21, 1988

[54] METHOD OF APPLYING COSMETICS TO A SUBSTRATE AND ARTICLE

[75] Inventors: Charles T. Fellows; George T. Brown, Jr.; Robert C. Haines, all of Dayton, Ohio

[73] Assignee: QMAX Technology Group, Inc., Dayton, Ohio

[21] Appl. No.: 867,199

[22] Filed: May 27, 1986

[51] Int. Cl.$^4$ .................. B05D 1/04; A61K 7/025; B32B 31/00

[52] U.S. Cl. ................... 427/27; 156/276; 427/385.5; 424/63; 424/64; 424/401; 424/408; 424/455; 424/490; 514/963

[58] Field of Search ............ 424/401, 63, 408, 64, 424/455, 490; 252/522 A, 522 R; 514/963; 156/276; 427/385.5, 27, 391

[56] References Cited

U.S. PATENT DOCUMENTS

| | | |
|---|---|---|
| 3,303,046 | 2/1967 | Chebiniak et al. .......... 252/522 A |
| 3,472,675 | 10/1969 | Gordon et al. .............. 252/522 A |
| 3,499,962 | 3/1970 | Wurzburg et al. .......... 252/522 A |
| 3,516,846 | 6/1970 | Matson ...................... 252/522 A |
| 3,565,559 | 2/1971 | Sato et al. .................. 252/522 A |
| 4,217,344 | 8/1980 | Vanlerberghe et al. ..... 252/522 A |
| 4,601,863 | 7/1986 | Shioi et al. ................. 252/522 A |

FOREIGN PATENT DOCUMENTS

| | | | |
|---|---|---|---|
| 50-070532 | 6/1975 | Japan ............ | 252/522 A |
| 54-055741 | 5/1979 | Japan ............ | 252/522 A |
| 55-085515 | 6/1980 | Japan ............ | 252/522 A |
| 58-143760 | 8/1983 | Japan ............ | 252/522 A |

*Primary Examiner*—Thurman K. Page
*Attorney, Agent, or Firm*—Wood, Herron & Evans

[57] ABSTRACT

A unique system for distributing and sampling cosmetics is disclosed. The cosmetics which are normally dry, are combined with a liquid carrier and film forming agent and deposited onto a substrate. The film forming agent acts to microencapsulate the cosmetic and lightly bond the cosmetic to the substrate. When the film forming agent dries, it protects the cosmetic. Thus, the cosmetic can be applied to a substrate and covered with a paperboard sheet. Access to the cosmetic can be provided by a tear strip. Greasy cosmetics, such as lipstick, can also be applied to a substrate according to the present invention. These cosmetics are first microencapsulated with gelatin and the formed microparticles are secondarily encapsulated with a film forming agent and deposited onto a substrate. This method permits cosmetics to be distributed through the mail and as magazine inserts and the like.

19 Claims, 1 Drawing Sheet

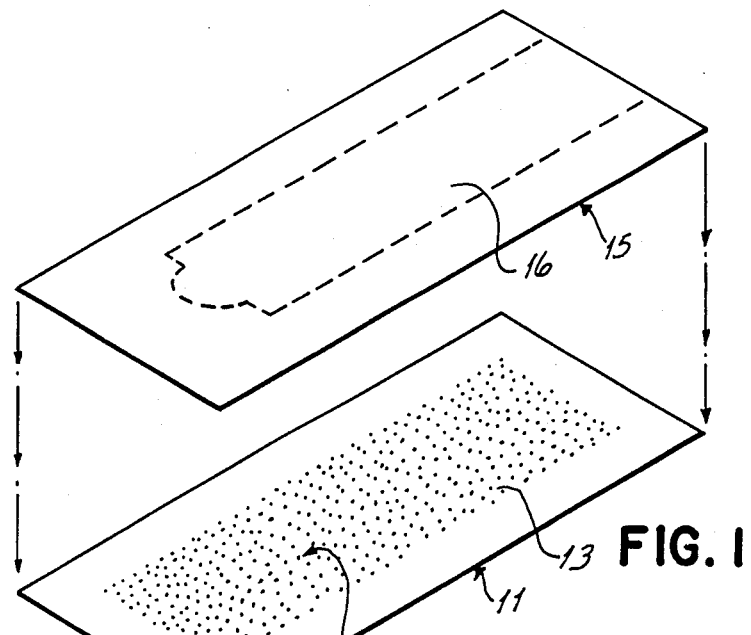
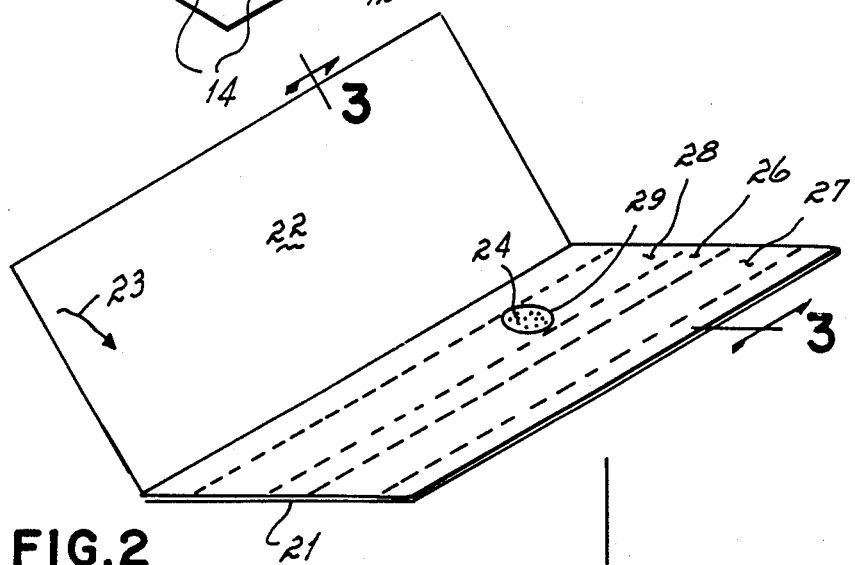
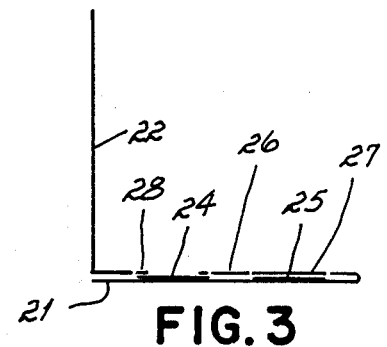

METHOD OF APPLYING COSMETICS TO A SUBSTRATE AND ARTICLE

BACKGROUND OF THE INVENTION

The present invention relates to cosmetics. More particularly the present invention relates to a method of applying cosmetics to a substrate such as paper stock, plastics, fabrics, or foils.

Further, the present invention relates to microencapsulated cosmetics deposited onto a substrate, suitable for mass distribution through the mails and the like.

Traditionally, cosmetics have been packaged in containers such as bottles, jars, flasks, boxes, and tubes. Cosmetic houses go to great expense in selecting a container type, style and design which provides a competitive advantage in gaining and keeping marketing elegance and appeal or identity of respective cosmetic products. They avoid the restaurant type mustard, ketchup, and sugar packets which would be crushed-open in the mail.

The fragrance houses and cosmetic manufacturers are also searching for new methods of promoting and of distributing cosmetics such as the highest quality, multicolored types in magazine inserts and or direct mailers. Providing cosmetic products in traditional packaging forms which would be carried via magazine inserts or direct mailers is either impossible or economically unattractive using current technology.

There is also a problem with traditional methods of demonstrating cosmetics at cosmetic counters. Due to the recent concern with communicable diseases, cosmetic wearers are unwilling to sample onto themselves the open cosmetics from a communal dispenser as is customary at a cosmetic counter. To overcome this concern, very small quantities of the cosmetics must be provided in sample packages. Again with current accepted methods this is cost prohibitive.

In the last few years designer houses creating fashionable fragrances have employed pull-apart, or scratch-open products containing printed areas utilizing microencapsulation techniques. Basically, fragrance oils, i.e. "perfumes", are transferred into an encapsulated form which is mixable with water. This is formulated into an aqueous vehicle delivery system which includes water soluble or colloidal binders. Thus the encapsulated fragrance is converted into a non-polluting vehicle type of printable ink or coating. The coating is normally applied as a thin film to a paper surface and an opposing surface is brought into contact with the still wet coating and the laminated areas allowed to dry. The fragrance ink acts as a dry mastik which adheres to both of the opposed paper surfaces, cementing them temporarily together. Co-adhesive strength of the connecting composition or thin coating is very poor. When the two opposing paper surfaces are pulled or jerked apart, the microencapsulation is ruptured and the fragrance is released. This provides a very economical means for fragrance houses to sample and to distribute samples of their fragrances via mass distribution methods. The action of opening becomes a memorable event to the senses.

Unfortunately, this technology cannot be easily transferred to cosmetics. Cosmetics typically are dry or cohesive powders or oily or emulsion type dispersions or easily meltable pastes, such as lipstick, which have a very defined appearance and feel. Any attempt to apply the cosmetic to a substrate for mass mailing must not bleed or leak or stain the substrate nor can the cosmetic itself be altered in its own color, feel or appearance. Unfortunately, the cosmetic cannot be directly applied to the substrate since it will, in the case of powders, simply fall off from the substrate, or in the case of a non-drying paste, remain tacky and rub off on everything it touches. Summertime shipping temperatures for mail or freight which can reach 150° F. and more can destroy such items.

Further, in order for a cosmetic to be attractive as possible when provided on a paper substrate, such as colorful and economical mailers, the cosmetic should be in a form suitable to be applied conveniently by means of using standard printing techniques.

To be printable, the cosmetic must be provided in a fluidized form. It is known to formulate a cosmetic such as blush as a liquid. This is discussed in Murphy et al, U.S. Pat. No. 4,337,859. The Murphy reference relates to one modern method of forming a molded cosmetic powder cake. In this method, the cosmetic is formed as a slurry of the cosmetic, a fatty alcohol and a vaporizable siloxane. This is heated, extruded or poured into a shaped receiver cavity and cooled to form a solidified cake of cosmetic. This is then dried in order to evaporate the siloxane carrier, yielding the proper texture.

The printing process is generally a very rapid process where the printed material frequently reverses direction around small rollers in order to control tension, tracking, flatness, and the like. This requires substantial adhesive strength in the coating applied to the substrate. The slurry of cosmetic disclosed in Murphy is simply deposited into a cavity where it is allowed to dry and set. Once dried, the cosmetic has relatively little adhesive strength and therefore this slurry would not adhere if it were to be printed as an "ink" in the form of a thin film onto a substrate. Accordingly, the material disclosed in Murphy is totally unsuitable for use in preparation of a cosmetic to be deposited onto a substrate.

SUMMARY OF THE INVENTION

The present invention is premised upon the realization that cosmetic forms can be formulated into a printable slurry which will adhere onto a substrate if the cosmetic is first surrounded, then microencapsulated by an appropriate film forming agent. The film forming agent, upon microencapsulating the cosmetic particulates provides for suitable "mother-liquor" phase-out adherence as the fluid evaporates upon the substrate but does not noticeably alter the appearance or texture of the cosmetic. The microencapsulating coating further permits the final (resultant) deposit of cosmetic to be easily removed from the substrate when wiped by the finger or a blush applicator.

In a preferred embodiment the present invention comprises the formation of a liquified mass of a cosmetic including a liquid carrier, such as ethanol, a film forming agent such as polyvinyl pyrrolidone and a plasticizer. This liquified mass is processed, then printed onto a substrate. The carrier volatiles are then evaporated, leaving behind the cosmetic microencapsulated by the film forming agent and also adhered to the substrate.

A cover sheet which includes a tear strip is adhered to the substrate with the tear strip located above the microencapsulated cosmetic. The dried film or polymer-rich skin surface results from drying of the cosmetic moiety through this surface, and conveniently also prevents the cosmetic from adhering to the tear strip or contacting force of the cover sheet. When the tear strip is pulled away or removed, the cosmetic area remains lightly adhered to the substrate and suitable for use as if no adhesive was present at all.

The present invention permits non-dry cosmetics, such as lipstick, to be deposited in a similar manner. However, the non-dry cosmetic must first be preliminarily microencapsulated as if to form a dry, particulate cosmetic. Such dry cosmetic particulates are then formed into a slurry including a liquid carrier, plasticizer, and film forming agent. This slurry is secondarily reencapsulated and concurrently deposited on a substrate to form a coating containing the microencapsulated particles of a non-dry cosmetic, yet having suitable handling characteristics.

This article can be used as a convenience sample at a cosmetic sales counter or it may be widely distributed as a magazine insert or as a direct mailer or with the Sunday newspaper in targeted sales areas or for promotional purposes.

The advantages of the present invention will be further appreciated in light of the detailed description and drawing in which:

BRIEF DESCRIPTION OF THE DRAWINGS

FIG. 1 is an exploded view of a preferred embodiment of the present invention.

FIG. 2 is a perspective view of an alternate embodiment of the present invention.

FIG. 3 is a cross sectional view taken at line 3—3 of FIG. 2.

DETAILED DESCRIPTION

According to the present invention, a cosmetic such as blush or lipstick is first compounded into a slurry which can then be printed onto a web or substrate by using standard printing techniques or coating methods. This slurry is applied or deposited onto a substrate. The slurry, upon drying, provides a microencapsulated cosmetic layer. The microencapsulation enables the cosmetic to adhere to the substrate at the same time, and does not adversely effect the desirable characteristics of the cosmetic.

To formulate the cosmetic slurry a dry, controlled-particulate-sized cosmetic is combined into a liquid carrier containing the dissolved or dispered a film forming agent as well as any additional or optional colorations or components such as plasticizers, vitamins, and the like.

The present invention utilizes a range of cosmetics such as the dry-powder blush and extending through non-dry, tacky cosmetics such as lipstick. The non-dry cosmetics must first be modified to a dry micro-particulate form for use in the present invention. The dry talc-based cosmetic powders can generally be used as purchased without the preliminary microencapsulation.

Cosmetic powders, as purchased, are dry particulate compositions including primarily an inert base or particulate component in combination with added plasticizers, coloring agents and fragrances. The inert components can include materials of the form of finely divided aluminum hydroxide, koalin, talc, mica, corn starch, calcium carbonate, calcined clays, silicas, aluminum oxide, aluminum silicate. Polymers such as nylons, polyolefins, and the like are also used. These are combined with suitable fragrances, sterilants, plasticizers, coloring agents and the like to provide the dry-cosmetics suitable for use in the present invention. The inert filler particulate portion in such cosmetic powders generally comprises about 70-90% of the "dry" cosmetic weight.

The film forming agent used to microencapsulate the dry particulate cosmetic is composed of one or more polymers which are soluble in the carrier and which during carrier evaporation will form into a relatively thin, weak coating around the cosmetic particulates and provide overall adhesive integrity for the cosmetic onto the substrate. The film forming agent can be natural or synthetic film forming agent such as nylons or polyamide, cellulose esters, starch esters, their ethers, or carboxylates, polyvinyl pyrrolidones, SBR block type copolymers, silicones as well as polyurethane including those formed from toluene diisocyanate precursors.

The film forming agent should be nontoxic, clear and not noticeably alter the appearance or properties of the cosmetic. The final film forming agent provides only weak adhesion between the particulate and to the substrate so that rubbing one's finger across the exposed microencapsulated cosmetic surface will thereby remove the cosmetic from its substrate. Upon drying, the film forming agent also serves to prevent the cosmetic evaporation interface from adhering to other contacted surfaces such as a cover sheet.

Preferably water or alcohol soluble polymers are used, particularly those which provide a transparent coating. The preferred film forming components are polyvinyl pyrrolidone and highly hydrolyzed polyvinyl alcohol. These are non-toxic and approved CTFA and F.D.A. cosmetics ingredients.

The cosmetic particulate and film former are combined with an effective amount of carrier to provide for a liquid slurry of cosmetic. The carrier can be any BP, USP, CTFA or pharmaceutically acceptable solvent which will at least partially dissolve and or colloidally disperse micelles of the film forming component. Suitable carriers may include water, alcohols suitable for fluidization of the composition (generally $C_2$–$C_{28}$), aromatic solvents, aliphatic solvents, N-methyl-2-pyrrolidone, butyrolactone, ketones, ethers, esters, volatile siloxanes, and mixtures. Particularly suitable are water ethanol, isopropanol, isoparrafin type naptha, cyclodimethicone and methyl ethyl ketone. A mixture of solvents may also be used. The solvent is combined with the film forming agent and cosmetic in an effective amount to provide a slurry which flows at application temperature. Preferably the fluidizing carrier is provided in a sufficient quantity to provide a suitable viscosity for the ease in printing of the cosmetic slurry.

When the carrier has a very low viscosity, a blend of carriers can be used. Particularly when the carrier is ethanol, or isopropanol, added water may be required to control or increase the viscosity and permit the cosmetic to remain in suspension.

The present invention can also optionally include plasticizers to maintain the feel of the cosmetic after the carrier is evaporated. Suitable plasticizers include fatty acid esters such as isopropyl myristate, isopropyl palmitate, magnesium stearate, as well as oils, glycerine, vitamin E, vitamin $D_3$, cholesteric esters, silicones, triglycerides, phytosterols and the like. Mixtures of plasticizers may be preferred to impart an appropriate feel and impart other desired characteristics. For example, the silicone plasticizers are excellent lubricants which assist in maintaining the applicator orifice clean and permit the cosmetic particles to fit tightly together once applied. Isopropyl myristate is a tacky plasticizer which promotes adhesion.

Preferably the cosmetic slurry will include about 30 to 65 parts by weight of cosmetic, from about 0.1 up to about 10 parts by weight of one or more plasticizers, from about 0.1 to about 5 parts by weight of film forming component (solids), and from about 1 to about 65 parts by weight of carrier. It is important to maintain the amount of film forming solids at an effective level relative to the amount of particulate material solids and related surface area in the cosmetic so as to provide also for effective adhesion of the cosmetic to a substrate. This provides for light adherence of the cosmetic to the substrate permitting the cosmetic to be easily removed from itself as well as from its own surface substrate for use by an individual utilizing their finger or commercial brush or foam applicator.

The slurry is formulated by combining the plasticizer and fluid carrier (excluding any water used to increase viscosity) in a high speed blender. The film forming component is then added and next added the cosmetic powder or particulates and finally any water needed to increase viscosity. This is incorporated without substantially altering the particle size of the cosmetics using standard blenders for example a Colloid Mill of the Graco type.

In a preferred embodiment of the present invention the slurry will include:

| Cosmetic Particulates | 49.0 Weight % |
|---|---|
| Iso-propyl myristate | .6 Weight % |
| Polydimethlsiloxane | .6 Weight % |
| Polyvinyl pyrrolidone | .6 Weight % |
| Ethanol | 48.2 Weight % |
| Water | 1.0 Weight % |

The slurry is formed up to by combining the components in the following order:
1. Alcohol
2. Isopropyl myristate
3. Polydimethlylsiloxane
4. Polyvinyl pyrrolidone
5. Cosmetic Powder Particulates
6. Water The cosmetic slurry can be applied to a variety of different substrates including paper, plastic, and fabric. Further, the slurry can be applied by various techniques including extrusion, spraying, including centrifugal and electrostatic types of spraying, and process for ink and transfer printing. In one embodiment the slurry is deposited onto the substrate with an airless (pressure) spray applicator at about 35 psi through a course nozzle. In another, the cosmetic and related fluidizing carrier may be passed through an electrostatic sprayer.

When a volatile carrier, such as ethanol is used, there is no need to actively drive off the carrier. Typically the high speeds and surface air flows encountered in a printing operation and the paper absorption will quickly cause the carrier to evaporate. When a less volatile carrier is employed, or for some reason, the slurry must set quickly, heat may be applied to the web either before or after application of the slurry. Specifically, heat ovens and lamps have been used to preheat the substrate and also the freshly applied cosmetic. Heating elements can be used in cooperation with the spray apparatus to heat the slurry and the atomizing air prior to atomization and deposition. Ovens are commonly used for curing inks.

The evaporative drying of the carrier leaves the coating of cosmetic deposited upon the substrate and also encapsulated by the film forming component. The film forming component coats the cosmetic micro-particles and also coats and adheres to the substrate. Generally, the thickness of the wall of the microcapsule will be from about 200 angstrom to up to 2-6 thousand microns. Preferably, this film former is water soluble or soluble in a common make-up remover such as cold cream or soapy water. This improves the cosmetic making it easier to remove.

As shown in FIG. 1 there is a preferred embodiment of the present invention where the cosmetic slurry is applied to a paper or plastic film or even a paperboard substrate to be used as a direct mailer or magazine insert. In this embodiment there is a base sheet or substrate 11. Printed onto a central portion 12 of the base sheet 11 is a narrower strip 13 of the cosmetic slurry.

The base may be transparent or can be the same color as the cosmetic. This would improve the appearance of the article as the cosmetic is removed. A peripheral area 14 of the base sheet 11 is uncoated by the slurry. After partial or substantial drying of the slurry, a cover sheet 15 is bonded to the base sheet so that the bonding occurs only at the peripheral area 14 according to the product design requirements.

The cover sheet 15 includes a suitably located perforated area tear strip 16 which, when the cover sheet 15 is bonded to the base sheet 11, is aligned over the strip 13 of cosmetic. The cover sheet prevents any unwanted or pre-use exposure of the cosmetic. It furthermore serves a sanitary function, preventing contamination of the sample.

To access the cosmetic the tear strip 16 is torn from the cover sheet 15 exposing the cosmetic strip 13, which in its current form, is microencapsulated and only lightly adhered to the base sheet 11. Since the cosmetic is protected by a polymer enriched dry skin film as well as by the encapsulation procedure beneath, it does not adhere to surfaces of the tear strip 16. The cosmetic structural adherence is controlled by controlling the amount of film forming agent solids to permit the end user of the cosmetic to easily wipe it from the supporting base sheet 11 and once applied to remove it from the users skin. This article is appropriate for inserting into magazines, and for uncontrolled handling and distribution by mail as well as for sanitary customer sampling as upon a cosmetic sale counter.

As shown in FIGS. 2 and 3, this invention can be practiced in a variety of different ways providing flexibility and permitting creativity. The article shown in FIGS. 2 and 3 also includes base sheet 21 which include a flap or cover 22 adapted to fold over base sheet 21 as indicated by arrow 23. Deposited on base sheet 21 are two strips 24 and 25 of the microencapsulated cosmetic of the present invention.

The strips 24 and 25 are covered by cover sheet 26. Cover sheet 26 includes two perforated portions 27 and 28 provided to align over strips 24 and 25 when sheet 26 is bonded to base sheet 21. Perforated portion 28 includes an aperture 29 which exposes a portion of cosmetic strip 24.

When used, the flap 22 is folded over cover sheet 26 protecting the cosmetic exposed at aperture 9. As soon as the user opens the flap, the cosmetic exposed at aperture 29 is visible and can be used immediately. This calls the users attention to the tear strips 27 and 28 encouraging her to remove the strips and sample the cosmetic.

This invention can be used in many different applications. The cosmetic can be deposited onto colored or transparent substrates as well as flat or shaped substrates. The cover sheet can be folded onto or glued to the substrate and likewise can be opague or transparent.

The present invention is also suitable for use with never-dry or paste cosmetics, particularly mascaras and lipsticks. Lipsticks are primarily emulsions which include high molecule weight oils (greases) along with fillers, plasticizers, fragrances, flavors and coloring agents. With such paste cosmetics there obviously would be no problem with expected levels of adherence to a substrate since they are naturally tacky. The problem encountered with these cosmetics is that they are designed to remain in this tacky state and to resist change. Accordingly, when such cosmetics are applied to a substrate and subsequently covered with a cover sheet, the cosmetic adheres to the cover sheet as well as to the substrate. This provides an article with a very unattractive, greasy, bleeding, "melting" or "spoiled" appearance.

To avoid this severe problem, the paste cosmetics are first made non-sticky by enclosing them within a non-sticky wall as microdroplets by microencapsulating in order to form dry, "leak-proof" and particulate cosmetics. The preliminary sizing of the micro-particulates by microencapsulation permits the cosmetics to be secondarily or subsequently microencapsulated by a variety of film forming solids which will also adhere to the substrate according to the present invention. This permits normally incompatible liquid, sticky, or paste cosmetics to be made useable with this method.

Preferably the preliminary encapsulation is conducted using a liquid crystal phenomenon or method known as "coacervation". According to the coacervation method, the non-dry, hydrophobic, oleophilic cosmetic, particularly such as a lipstick, is quickly heated and melted forming a liquid. This is promptly dispersed into slurry form of microdroplets within a coacervating solution comprising an aqueous sol of a coacervatable colloid at a temperature above the phase change or the gel point of the coacervatable colloid. A coacervating inducing agent is then added, where upon a film of the coacervate deposits around each of the microparticulates of the cosmetic.

The term "coacervatable colloid" is intended to refer to a gellable hydrophilic colloid which, in an aqueous sol with the addition of a coacervating induction agent, forms both a liquid colloid rich and colloid poor phase. The colloid rich phase deposits about any convenient nuclei which in this case are the micro-oleophilic particulates. The colloid poor phase constitutes the equilibrium liquid, the mother liquid.

Suitable, gellable, hydrophilic colloids include gelatin, agar-agar, albumen, alginates, casein, pectins, starch and fibrinogen, the preferred colloid being gelatin. The primary thickness of the coacervate membrane enclosing the oleophilic cosmetic particles will depend on the amount of colloid provided (available) for formation of the coacervate and the size of, or surface area of cosmetic particles being covered and encapsulated. The secondary thickness is the added encapsulation provided by the ink formulation used.

The term "coacervating agent" refers to materials capable of initiating or inducing the separation into a colloid rich phase and a colloid poor phase from an original homogeneous or single phase colloidal sol. Such substances contemplated by the term "coacervating agent" include aqueous solutions of electrolytes including organic and inorganic salts; for example salts having alkali or alkali-metal cations such as sodium, ammonium, magnesium and potassium, also organic or inorganic anions such as sulfate, phosphate, acetate, formate, and also liquid systems which are water soluble and in which the coacervating colloid is less soluble than in water, for example gum arabic and carrageenan. A critical temperature as well as concentration exists for each coacervating agent below which coacervation will not occur. The pH is important and should be neutral to slightly acidic. These parameters are generally well known to those of ordinary skill in the art.

A thickening agent such as acacia, tragacanth, methyl cellulose, carboxy methyl cellulose, and magnesium aluminum silicate as well as other thickening agents such as polyglycol, glycerine, and syrups can be added provided they do not affect the desired application properties.

Preferably, a gelatin sol is combined with the cosmetic both at about 55° C. The coacervating agent, preferably gum arabic or carrageenan at about 55° C. is then added under constant and vigorous stirring. The temperature is maintained at approximately 55° C. through this processing period including mechanical sizing, dispersing and mixing. Coacervation enshrouding should occur rapidly on contact of the gelatin sol to the cosmetic particulate dispersed emulsion when initiated by the coacervating agent. The temperature of the coacervating solution and equipment is then allowed to go down to room temperature (taking about 30 minutes) and then is subsequently quick chilled to about 10° C. to gel the coacervate. A cross-linking agent such as formaldehyde or more preferably gluteraldehyde is added to the now "gelled" coacervate micro-walls in order to harden and to insolublize the coacervate. The hardened coacervate coated product is then filtered, washed, and dried to yield small particles of encapsulated emulsion.

The ultimate particle size of the coacervate product is dependent in part on the degree of the core particulates, their degree of dispersion or the overall size of the emulsion agglomerated cosmetic particles residing in the coacervate sol slurry. The particle size is enlarged slightly as a function of the applied thickness of the coacervate wall thickness of coating. Also of importance in this regard is the degree of fineness of the ultimate particles in this dispersion of the cosmetic and coacervative colloid, and the severity of the reactions from the coacervating agent. The more complete and rapid the mixing, the smaller are the formed "core" droplets that are presented as nuclei about which the coacervate will form, and hence the thinner will be the coacervate wall for a given amount of coacervate polymers. These nuclei are preferably in the range from 15 to 200 microns in diameter although they can be manufactured up to 5000 microns for requirements of some applications.

The finally treated coacervate, (once separated and dried), can be treated as dry plastic powders or particulates containing the cosmetic. These formed "microencapsulated" particles are then compounded as described before for coatings which are then coated onto substrates in the same manner that the dry cosmetic was coated onto its substrate as previously described. In other words, a cosmetic slurry of the microencapsulated particles is formed by combining the microencapsulated particles with a liquid carrier, a film forming agent, as well as optional components such as plasticizers, vitamins, and the like.

As with the dry cosmetics, the microencapsulated particles should comprise 30 to 65 PBW by weight of the slurry. The plasticizer should comprise from about 0.1 PBW up to about 10 PBW by weight. The film forming component should comprise from about 0.1 up to about 5 PBW by weight of the final slurry on a solids basis and the carrier should be form 1 to 65 PBW of the slurry. Further, the amount of filmforming solids has to be maintained at an effective level relative to the microencapsulated particles solids to provide for the encapsulation of these cosmetic microcapsules simultaneously with the adhering of the microencapsulated cosmetic particles to the substrate.

The following table presents the preferred range as parts by weight of the components for preliminary testing of the microencapsulation properties:

|  | Weight Ranges | Preferred |
| --- | --- | --- |
| Cosmetic as received | 35–65 Parts | 49 Parts |
| Gelatin | 1–15 Parts | 7 Parts |
| Coacervating Agent | 1–15 Parts | 7 Parts |
| Gluteraldehyde (50%) | 0.1–8 Parts | 1 Parts |
| Water | 60–90 Parts | sufficient to provide coacervation |

The invention will be further appreciated in light of the following detailed example in which commercially available "Charles of the Ritz" brand of lipstick is formed into a microencapsulated droplet slurry than filtered to a damp articulated "presscake" of microcapsular material which can be dried. This can be subsequently redispersed in a thin microencapsulated form according to the method of the present invention with additional film forming agent which also permits its simultaneous adherence to a substrate and which also prevents it from subsequently adhering to a cover sheet due to the evaporating concentrating and filming of the polymer at the air-drying interface on the exposed surface. This dried film resists adhesion to the adjacent dry paper surface.

EXAMPLE

To a beaker, add 500 mls of distilled water and 10 grams of gelatin. Heat quickly to 50° C. under agitation to put the gelatin into solution. At as soon as the solution is complete, promptly adjust pH to 7.0 with a solution of NaOH. Maintaining a temperature of 50° C., add 1 ml of 70% sorbitol solution. Heat 100 gms of Charles of the Ritz lipstick to 55° C.

Under slow agitation, add the heated (melted) cosmetic into the heated gelatin solution. Slowly increase the energy input of agitation to reduce the surface areas of the cosmetic droplets to desired overall droplet size. When the desired droplet size is reached, the gelatin is coacervated by phasing out the gelatin onto the droplets by adding 50 mls of a 2% solution of carrageen in distilled water. (This may be hot or cold.).

Next, (after coacervation), remove heat and continue to cool down with agitation until room temperature is reached (about 30 minutes for 600 ml). Cool to 10° C., in about 5 minutes, in an ice bath, maintaining agitation. Add 3 ml of 50% gluteralde-hyde. Maintain 10° C. for another ½ hour then allow the process to slowly come up to room temperature. Wash and filter the encapsulated cosmetic material three (3) times to assure cleanliness for body contact uses.

The following table discloses the preferred remaining components used to microencapsulate the preliminarily microencapsulated cosmetic particles:

|  | Parts by Weight | Preferred |
| --- | --- | --- |
| Isopropyl myristate | .1–5 | .6 |
| Polydimethlsiloxane | .1–5 | .6 |
| Polyvinyl pyrrolidone | .1–5 | .6 |
| Ethanol | .1–65 | 48.2 |
| Water (as needed) | 1.0–65 | about 1.0 |

The slurry is formed in the same manner as previously described in the first description when using the dry cosmetic, and is then printed onto or applied to a substrate in the same manner.

Thus according to the present invention, cosmetics that are dry, particulate cosmetics as well as tacky or pasty cosmetics, can be similarly applied to or be provided on a paper, plastic, fabric, or foil substrate covered with a removable covering sheet or windowing area suitable for use as a mass mailer. Further, both solid and tacky cosmetics can be simultaneously provided side-by-side in the same "mass-mailer". For example, with embodiment shown in FIGS. 2 and 3, strip 27 could be blush which is normally a dry particulate cosmetic. Strip 28 could be lipstick. These two incompatible materials can be held on a single substrate without commingling.

Thus having disclosed our invention, we claim:

1. A method of applying a particular cosmetic to a substrate comprising:
   forming a slurry of microcapsules of said cosmetic by combining said cosmetic, a liquid carrier and a film forming component, said film forming component provided in an amount effective to microencapsulate and bind said cosmetic to a substrate when the carrier evaporates;
   adding a plasticizer in an amount effective to prevent said film forming component from altering the texture of said cosmetic after the carrier has evaporated;
   applying said slurry to said substrate;
   evaporating the carrier to thereby form a microencapsulated cosmetic adhered to said substrate wherein said cosmetic comprises inert particulate matter, coloring agents and fragrances and wherein said effective amount of the film forming component is less than about 12% based on the total of said film forming component on a solid basis and said inert particulate matter.

2. The method claimed in claim 1 wherein said film forming component is selective from the group consisting of polyvinyl pyrrolidone, polyvinylalcohol, polyurethane, SBR block copolymers, cellulose, methylcellulose, silicone and mixtures thereof.

3. The method claimed in claim 1 wherein said plasticizer is selected from the group consisting of fatty acid esters, triglycerides, glycerine, vitamin E, vitamin $D_3$, silicones, cholesteric esters, phytosterols and mixtures thereof.

4. The method claimed in claim 1 wherein said carrier is added in an amount effective to provide a slurry having a viscosity from about 2 to about 800 cps.

5. The method claimed in claim 4 wherein said carrier is selected from the group consisting of $C_2$–$C_{28}$ alcohols, aromatic solvents, aliphatic solvents, ketones, ethers, volatile siloxanes, water N-methyl-2-pyrrolidone and mixtures thereof.

6. The method claimed in claim 5 wherein said carrier is selected from the group consisting of water, ethanol, isopropanol, isoparrafin naptha, cyclodimethicone, and mixtures thereof.

7. The method claimed in claim 1 wherein said slurry is formed by adding said plasticizer to said carrier with agitation; and
adding said film forming component to said carrier and plasticizer with agitation to form a film forming component containing mixture; and
adding said cosmetic to said film forming component containing mixture with agitation to form encapsulated particles of cosmetic and subsequently homogenizing said final mixture without reducing the particle size of said cosmetic.

8. The method claimed in claim 1 wherein said slurry is extruded onto said substrate.

9. The method claimed in claim 1 wherein said slurry is sprayed onto said substrate.

10. The method claimed in claim 9 wherein said slurry is electrostatically sprayed onto said substrate.

11. The method claimed in claim 1 wherein said slurry is deposited onto said substrate with a printing press.

12. The method claimed in claim 1 wherein said substrate is paper.

13. A method of applying a non-dry cosmetic to a substrate comprising:
forming discrete microencapsulated particles of said non-dry cosmetic;
forming a slurry by combining the discrete particles of said cosmetic with a liquid carrier and a film forming component, said film forming component provided in an amount effective to microencapsulate said discrete particles and bind said particles to a substrate when said carrier evaporates;
wherein said slurry comprises 30-65 parts by weight microencapsulated particles, 0.1-10 parts by weight plasticizer, 0.1-5 parts by weight film forming component, and 1-65 parts by weight carrier;
applying said slurry to said substrate wherein said substrate comprises a first sheet;
evaporating the carrier to thereby form microencapsulated microcapsules of said cosmetic adhered to said substrate
covering said sheet with a cover sheet co-extensive with said first sheet whereby film forming component acts to adhere said microencapsulated particles of said non-dry cosmetic to said first sheet and acts to prevent microencapsulated particles of said non-dry cosmetic from adhering to said cover sheet.

14. The method claimed in claim 13 wherein said discrete particles of said non dry cosmetics are gelatin encapsulated.

15. A method of applying particulate cosmetics to a substrate wherein said cosmetic comprises inert particulate matter, coloring agents and fragrances, said method comprising:
forming a slurry of microcapsules of said cosmetic by combining said cosmetic, a liquid carrier and a film forming component, said film forming component provided in an amount effective to microencapsulate and bind said cosmetic to a substrate when said carrier evaporates wherein said substrate is a first sheet;
adding a plasticizer in an amount effective to prevent said film forming component from altering the texture of said cosmetic after said carrier has evaporated;
applying said slurry to said first sheet;
evaporating the carrier to thereby form a microencapsulated cosmetic adhered to said first sheet;
binding a second sheet to said first sheet with said microencapsulated cosmetic between said first sheet and said second sheet wherein said film forming component maintains microencapsulated cosmetic adhered to said first sheet but prevent said microencapsulated cosmetic from adhering to said second sheet.

16. The method claimed in claim 15 wherein said cosmetic comprises 70-90 percent inert particulate matter and said slurry comprises about:

| | |
|---|---|
| Cosmetic | 35-65 PBW |
| Film Forming Component | .1-5 PBW |
| Carrier | 1-65 PBW |
| Plasticizer | .1-10 PBW |

17. The method claimed in claim 16 comprising:

| | |
|---|---|
| Cosmetic | 49.0 PBW |
| Polyvinyl pyrrolidone | .6 PBW |
| Ethanol | 48.2 PBW |
| Water | 1 PBW |
| Polydimethlysiloxane | .6 PBW |
| Isopropyl myristate | .6 PBW |

18. The method claimed in claim 15 wherein said slurry is deposited on a central portion of said substrate.

19. The method claimed in claim 15 wherein said cover sheet includes a tear strip and said tear strip is centered over said cosmetic.

* * * * *